(12) United States Patent
Losordo et al.

(10) Patent No.: US 10,743,895 B2
(45) Date of Patent: Aug. 18, 2020

(54) CLOT RETRIEVAL DEVICE FOR ISCHEMIC STROKE TREATMENT

(71) Applicant: NeuroVasc Technologies, Inc., Laguna Hills, CA (US)

(72) Inventors: Michael Losordo, San Juan Capistrano, CA (US); Jianlu Ma, Irvine, CA (US)

(73) Assignee: Neuro Vasc Technologies Inc., Laguna Hills, CA (US)

( * ) Notice: Subject to any disclaimer, the term of this patent is extended or adjusted under 35 U.S.C. 154(b) by 252 days.

(21) Appl. No.: 15/991,931

(22) Filed: May 29, 2018

(65) Prior Publication Data

US 2018/0344337 A1 Dec. 6, 2018

Related U.S. Application Data

(63) Continuation of application No. 15/614,053, filed on Jun. 5, 2017, now Pat. No. 9,993,257.

(51) Int. Cl.
*A61B 17/221* (2006.01)
*A61B 17/22* (2006.01)

(52) U.S. Cl.
CPC .... *A61B 17/221* (2013.01); *A61B 2017/2215* (2013.01); *A61B 2017/22081* (2013.01)

(58) Field of Classification Search
CPC ............. A61F 17/221; A61F 17/32056; A61B 2017/2212
See application file for complete search history.

(56) References Cited

U.S. PATENT DOCUMENTS

| 8,529,596 B2* | 9/2013 | Grandfield | ....... A61B 17/32072 606/127 |
| 8,777,976 B2* | 7/2014 | Brady | .............. A61B 17/22031 606/127 |

(Continued)

FOREIGN PATENT DOCUMENTS

| EP | 1 411 859 A1 | 4/2004 |
| EP | 2 848 211 A1 | 3/2015 |

(Continued)

OTHER PUBLICATIONS

Office Action dated Apr. 17, 2019 for corresponding Australia Application No. 2017324159.

(Continued)

*Primary Examiner* — Julie A Szpira
(74) *Attorney, Agent, or Firm* — Raymond Sun

(57) ABSTRACT

A clot removal device has a segment that has two main struts that serve as a frame for holding a plurality of secondary struts. Each of the two main struts has a proximal end that is connected at a proximal point of the segment and extends along a generally circumferential path, with each main strut terminating at a separate connecting point that is distal from the proximal point. The connecting points are connected to each other to form a generally tubular structure defining an inner lumen. The plurality of secondary struts forms a lattice of cells, with each cell surrounded by four secondary struts. Two generally straight distal struts are connected to the lattice of cells at a distal end of the segment, and are connected to each other to form a distal point. A distal opening is defined by the cells adjacent the distal struts, the distal opening communicating with the lumen and terminating at the proximal point.

11 Claims, 5 Drawing Sheets

(56) References Cited

U.S. PATENT DOCUMENTS

| | | | |
|---|---|---|---|
| 2003/0204202 A1 | 10/2003 | Palmer | |
| 2007/0288054 A1* | 12/2007 | Tanaka | A61B 17/221 606/200 |
| 2009/0292297 A1* | 11/2009 | Ferrere | A61M 25/09025 606/127 |
| 2011/0009875 A1* | 1/2011 | Grandfield | A61B 17/221 606/127 |
| 2011/0009950 A1* | 1/2011 | Grandfield | A61F 2/91 623/1.16 |
| 2013/0079796 A1* | 3/2013 | Slee | A61B 17/221 606/127 |
| 2014/0121672 A1* | 5/2014 | Folk | A61B 17/221 606/127 |
| 2014/0276922 A1* | 9/2014 | McLain | A61B 17/221 606/128 |
| 2015/0250497 A1 | 9/2015 | Marks | |
| 2016/0015403 A1* | 1/2016 | Nguyen | A61B 17/221 606/127 |
| 2016/0113665 A1* | 4/2016 | Brady | A61B 17/12109 606/127 |
| 2016/0192956 A1* | 7/2016 | Brady | A61B 17/22031 606/159 |
| 2016/0192957 A1* | 7/2016 | Okada | A61B 17/221 606/127 |

FOREIGN PATENT DOCUMENTS

| | | |
|---|---|---|
| EP | 2 959 853 A1 | 12/2015 |
| WO | WO2012/106657 A2 | 8/2012 |

OTHER PUBLICATIONS

Supplemental Search Report dated Jan. 20, 2020 for corresponding European Application No. 2EP 17 84 9332.

PCT International Preliminary Report dated Mar. 12, 2019 for corresponding PCT/US2017/049155.

* cited by examiner

CLOT RETRIEVAL DEVICE FOR ISCHEMIC STROKE TREATMENT

RELATED CASES

This application claims priority from U.S. Provisional Application Ser. No. 62/384,678, filed on Sep. 7, 2016, the contents of each of which are incorporated by this reference as if fully set forth herein in their entirety.

BACKGROUND OF THE INVENTION

Field of the Invention

The present invention generally relates to devices and methods useful for clot retrieval, and removal devices to treat, among other things, ischemic stroke.

Description of the Prior Art

Currently, the FDA-approved treatment options for an acute ischemic stroke include intravenous (IV) delivery of clot dissolving medicine and mechanical thrombectomy.

For treatment use, clot dissolving medicine, such as the thrombolytic agent (Tissue Plasminogen Activator (t-PA)), is injected into the vasculature to dissolve blood clots that are blocking blood flow to the neurovasculature. Intravenous t-PA is currently limited in use because it must be used within a three-hour window from the onset of a stroke and can result in an increased risk of bleeding. This standard of care leaves room for upgrade, and is only the appropriate approach to treatment for a limited class of individuals, groups and temporally-limited exigent cases.

A second option includes the use of mechanical thrombectomy devices. Such devices are designed to physically capture an embolus or clot, and to remove it from the blocked vessel, thereby restoring blood flow. The major advantage of the mechanical thrombectomy device is it can expand the treatment window from three hours to over ten hours.

Some existing mechanical thrombectomy devices used for increasing blood flow through an obstructed blood vessel include: 1) a filter trap designed and built to collect and remove emboli; 2) a cork-screw guidewire-like device to retrieve embolus; and 3) a stent-like device connected to a delivery wire to retrieve embolus. All of these devices suffer from certain disadvantages.

First, filter-type thrombectomy devices tend to be cumbersome and difficult to deliver and deploy, and a larger-profile guide catheter may be needed to fully remove the embolus. In addition, it is difficult to coordinate precise and predictable movement to position the device properly in the vessel. The device can drift within the vessel, twist, or not be adequately conforming to the vessel wall and, therefore not effective for removing embolus.

Cork-screw guidewire devices can only capture and remove emboli that are firm, or subject to certain mechanical variables such as being held together by itself as one piece. Cork-screw guidewire devices are not effective in removing particulate matter that may be scattered or broken up.

Stent-like mechanical thrombectomy devices are not capable of capturing small emboli that break off from a large embolus (if any), and can lead to complications such as the blockage of distal smaller vessels, vessel dissection, perforation, and hemorrhage arising as a result of over-manipulation in the vessel.

The disadvantages common to all of the devices described above include, for example: 1) the device may capture an embolus, but then lose grasp of it and migrate/deposit it incidentally into another area of the neurovasculature, creating the potential for a new stroke in a different part of the neurovasculature; 2) the device is not capable of capturing small embolus breaking off from the larger embolus and preventing it from migrating to a more distal area of the neurovasculature; 3) the relative large device profile prevents these devices from treating the distal smaller diameter vessels; and 4) risk of sICH (symptomatic Intra-cerebral Hemorrhage) after intra-arterial clot removal in acute stroke patients.

Other flaws in the current mechanical thrombectomy designs include poor visibility/radiopacity, lack of variation in the delivery portion to enhance and improve deliverability, and lack of coatings or modified surface textures on the treatment portion to enhance embolus affinity, etc. In conclusion, there is a great need for improved devices, systems, and methods for restoring blood flow through a blood vessel. None of the existing medical mechanical thrombectomy devices address all necessary needs to date.

SUMMARY OF THE DISCLOSURE

The present invention is directed to a method and devices for removing clots, emboli and other luminal blockages from a blood vessel.

A method for removing a clot or embolus from a blood vessel according to the present invention includes providing a clot removal device having a segment that has two main struts that serve as a frame for holding a plurality of secondary struts. Each of the two main struts has a proximal end that is connected at a proximal point of the segment and extends along a generally circumferential path, with each main strut terminating at a separate connecting point that is distal from the proximal point. The connecting points are connected to each other to form a generally tubular structure defining an inner lumen. The plurality of secondary struts forms a lattice of cells, with each cell surrounded by four secondary struts. Two generally straight distal struts are connected to the lattice of cells at a distal end of the segment, and are connected to each other to form a distal point. A distal opening is defined by the cells adjacent the distal struts, the distal opening communicating with the lumen and terminating at the proximal point. The clot removal device is delivered to the location of the clot or embolus in the blood vessel, and the segment is expanded at the location of the clot or embolus. The clot or embolus is caught in or engaged by the segment, and the segment is withdrawn with the engaged clot or embolus.

The clot removal device of the present invention can also include a second segment having two second segment main struts, each second segment main strut having a distal end and a proximal end, with the proximal end of each second segment main strut connected to a separate connecting point from the first segment, and with the distal ends of the second segment main struts joined at a second segment connecting point. A plurality of second segment secondary struts form a lattice of second segment cells, with each second segment cell surrounded by four second segment secondary struts. Two generally straight second segment distal struts extend distally from the distal end of the second segment cells, each second segment distal strut having a proximal end that is connected to each other to form a tip, and with a second segment distal opening defined adjacent the tip.

The clot removal device of the present invention can further a third segment that is identical to the first segment, with the proximal point of the third segment joined to the second segment connecting point.

The clot removal device of the present invention can also include a fourth segment that is identical to the second segment, with the proximal end of each fourth segment main strut connected to a separate third segment connecting point.

The clot removal devices of the present invention provide numerous benefits. First, the connecting points can allow for articulation or bending of the segments. This articulation can allow for independent motion of the segments, so that each segment can maintain its geometry at the bent configuration without buckling, hence maintaining better clot retention.

Second, the segments are joined along the outer diameter of the segments at the connecting points, and not along the central/longitudinal axis. When the clot removal device is bent, there is no force pulling the segments towards the center of the vessel, so that geometrical buckling is again prevented. When the clot removal device is pulled in tension, the device expands so that integration with the clot is maintained or increased. Therefore, the outer surface of the segments will always maintain contact with the clot and vessel wall, resulting in better clot retention.

Third, the struts comprising the joined segments may be larger than the other struts. The larger struts maintain the column strength when the clot removal device is at its compacted state. This can improve the ability to move the clot removal device through a catheter by pushing on the proximal end of the device without axial buckling. When the segments are deployed and engage the blood clot, the larger struts maintain the structural integrity of the clot removal device and minimize the geometry distortion and buckling, thereby providing better clot retention.

Fourth, the segmented or articulating clot removal device can help to improve clinical outcome post clot retrieval by reducing embolization of unaffected territory or distal emboli due to improved clot retention.

DETAILED DESCRIPTION OF THE PREFERRED EMBODIMENTS

Figure 1:
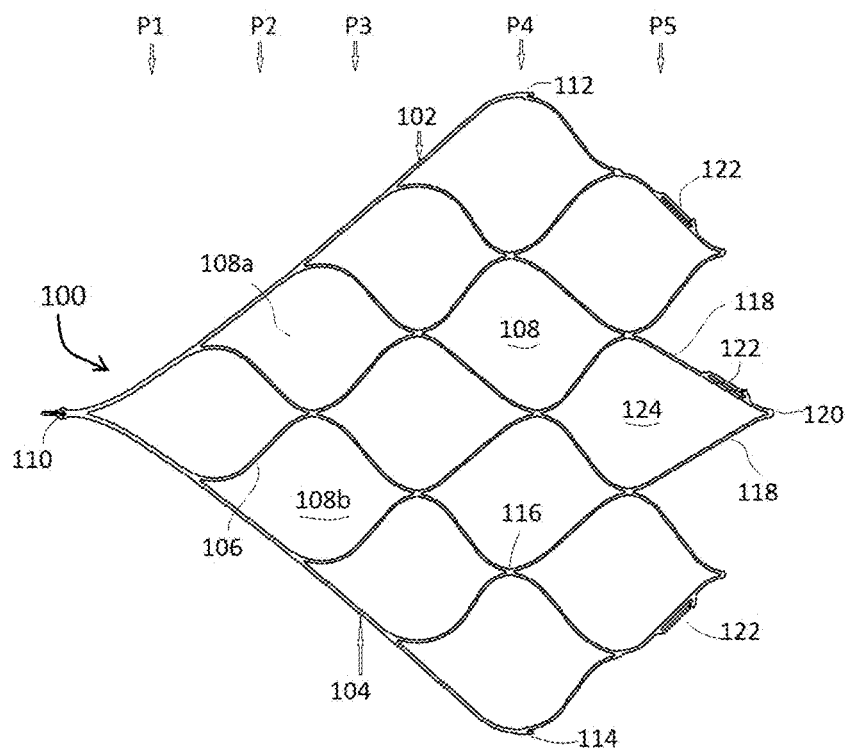
FIG. 1 is a two-dimensional view of a segment for a clot removal device according to a first embodiment of the present invention shown with the segment flattened.

The following detailed description is of the best presently contemplated modes of carrying out the invention. This description is not to be taken in a limiting sense, but is made merely for the purpose of illustrating general principles of embodiments of the invention. The scope of the invention is best defined by the appended claims.

The present invention is directed to a device for removing emboli and other luminal blockages. The device includes one or more expandable clot removal segments that are joined to either another clot removal segment or to a delivery wire. During treatment, the expandable segment(s) can be positioned within or distal to an embolus or clot within a blood vessel and then transitioned into an expanded state. In certain embodiments, the expandable segment's normal state is the expanded configuration, and the expandable segment is compacted and delivered to the treatment site in the compacted configuration through a delivery sheath, guide catheter, or microcatheter. The expandable segment is deployed from the delivery sheath, guide catheter or microcatheter, which causes it to return to its normal expanded profile by the elastic energy stored in the device. Expansion of the expandable segment engages it with the emboli or clot at the blockage. After expansion, the expandable segment and the emboli engaged with the expandable segment are removed from the blood vessel. Furthermore, aspiration/vacuum suction can be applied through the lumen of the access catheter lumen to prevent clots from breaking off and flowing downstream.

Devices of the present invention are suitable for removal of blockages in body lumens, and are particularly well-suited for removal of thrombi, emboli, or atheroma in the vasculature, including those in arteries and veins. It is understood that the dimensions of the device may be modified to suit a particular application. For example, devices of the invention used for treatment of deep vein thrombosis may have a larger cross-section than devices of the invention used for treatment of brain ischemic.

Compared with existing mechanical thrombectomy devices, the unique device design included in this invention has the following advantages. First, the clot removal device of the present invention is constructed by individual segments that can achieve a variable length by repeating the segments. Second, the connecting points for connecting each segment can allow for articulation or bending of the segments and also allow for independent motion of the segments in the tortuous vasculature, where the device diameter will not be reduced when it is bent, thereby allowing constant contact between the segment and blood vessel during use. Third, the segments are joined along the outer diameter of the retriever, and not along the central axis, thereby making it easy to bend and to conform to the vasculature. Fourth, the struts comprising the connecting points can be larger than the other struts, thereby improving the ability to move the clot removal device through a catheter by pushing on the proximal end of the clot removal device, and ensuring that there is no axial bulking. Fifth, the segments can have different diameters, and the struts within a segment can have different thickness, along the longitudinal axis. For example, the proximal segments can have larger diameters than the distal segments, or the distal segment can have a larger diameter than the proximal segment Sixth, the segments can be opposed by 180 degrees, or connected in a helix or in multiple helices around its circumference to create a noncentrosymmetric structure with auxetic properties. Seventh, the segments can be marked with coils, tubes, wires or other markers made of radiopaque, or x-ray blocking, materials such as platinum, gold, or other dense materials. Eighth, the clot removal device can be combined with the use of aspiration or vacuum pressure to assist in clot or emboli retrieval.

Thus, the device described in the present invention overcomes the shortcomings of the existing technologies and can be delivered to the target vasculature smoothly, can be retrieved safely, and can remove the entire embolus or clot with fewer passes. In use, the mechanical thrombectomy device described in the present invention can be compacted to a low profile and loaded onto a delivery system and delivered to the target location in the vessel by a medical procedure such as through use of a delivery catheter. The mechanical thrombectomy device can be released from the delivery system when it reaches the target implant site and expanded to its normal expanded profile by the elastic energy stored in the device (self-expandable device).

As for the relative position of the expandable treatment member in relation to the embolus or blood clot, it can either be deployed at the site of the embolus, or deployed distal to the embolus. In dealing with a long embolus, the expandable treatment member can also be used to remove the embolus from the proximal portion to the distal portion with multiple passes, until the entire embolus is removed.

The clot removal device of the present invention can also be used in other parts of the body to retrieve blockages, and to clear lumens.

Figure 2:
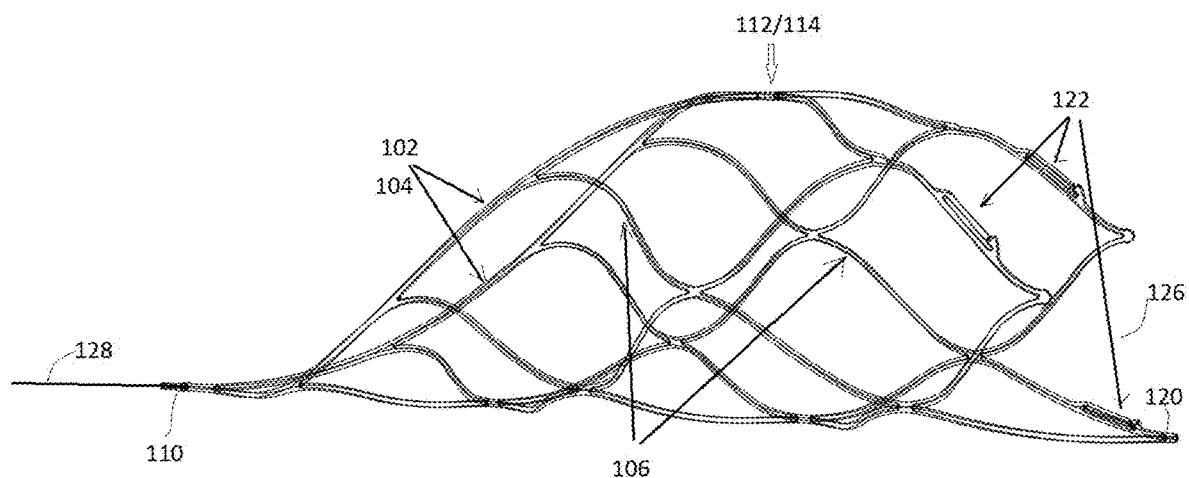
FIG. 2 is a three-dimensional view illustrating the segment of FIG. 1 with the segment connected at its connecting points.

Turning now to the drawings, FIGS. 1-2 illustrate a segment 100 for a clot removal device for removing emboli and other luminal blockages according to the present invention. The clot removal device can have one or more segments 100. The segments 100 can be made from one piece or multiple pieces of Nitinol super elastic sheet material or Nitinol super-elastic alloy tubing. It can also be made from other biocompatible materials that exhibit super-elastic or shape memory properties. The segments 100 can be made by laser cutting, mechanical machining, chemical machining, electrochemical machining, EDM, braiding and related techniques known to those skilled in the art.

The segment 100 has two main struts 102 and 104 that serve as a frame for holding or supporting a plurality of secondary struts 106. The secondary struts 106 are arranged into a pattern to form a lattice of cells 108. The two main struts 102, 104 originate from a proximal point 110 and extend along a generally straight segment in its flattened two-dimensional orientation as shown in FIG. 1. Each main strut 102 and 104 terminates at a connecting point 112 and 114, respectively.

Each secondary strut 106 has a straight section with opposite ends that are slightly curved in opposite directions so as to form an S-shape. The secondary struts 106 are joined at connection points 116 to form cells 108 that have a tear-drop-like shape due to the S-shaped configuration of the secondary struts 106. Each cell 108 is surrounded by four secondary struts 106. Each cell may also be surrounded by six, eight, or ten struts. Two generally straight distal struts 118 are connected to the secondary struts 106 at the distal end of the segment 100, and they are connected to each other to form a distal point 120. The distal struts 118 may also be curved. A distal opening 126 (see FIG. 2) is defined by the cells 108 and 124 adjacent the distal struts 118.

When the connecting points 112 and 114 are joined or connected, the segment 100 forms a tubular structure that defines a lumen. The distal opening 126 communicates with the lumen and the lumen terminates at the proximal point 110.

In the embodiment in FIG. 1, the segment 100 has four secondary struts 106 extending from each main strut 102 and 104, and the resulting lattice of cells 108 defines a row of four cells 108 along each main strut 102 and 104. The second cell (e.g., 108a and 108b) along each of these rows is the beginning cell for another row of four cells that extends perpendicular to the two rows along the main struts 102 and 104. A final distal cell 124 is defined by two secondary struts 106 and the two distal struts 118.

Another way to view this lattice is that the connected secondary struts 106 that extend from the main struts 102 and 104 define waveforms. For example, the proximal-most secondary struts 106 extending from the main struts 102 and 104 each define the beginning of a first waveform of four secondary struts 106, the second proximal-most secondary struts 106 extending from the main struts 102 and 104 each define the beginning of a second waveform of four secondary struts 106, the third proximal-most secondary struts 106 extending from the main struts 102 and 104 each define the beginning of a third waveform of three secondary struts 106, and the fourth or final proximal-most (or the distal-most) secondary struts 106 extending from the main struts 102 and 104 are the only secondary strut 106 that connects with the third waveform.

Yet another way to view this lattice is that there are five columns of cells 108, with a first proximal-most column P1 having one cell 108, a second proximal-most column P2 having two cells 108, a third proximal-most column P3 having three cells 108, a fourth proximal-most column P4 having four cells 108, and a fifth proximal-most (or the distal-most) column P5 having three cells, with two cells 108 and the distal cell 124.

The segment 100 may be marked with coils, tubes, wires or other markers made of radiopaque, or x-ray blocking, materials such as platinum, gold, or other dense materials. As an example, radiopaque marker attachments 122 can be provided on any of the struts 102, 104, 106 or 118. These markers can be made of Ta, Pt, W, Pt—W, or Pt—Ir alloys for radiopacity, and from radiopaque coils or markers. The function of the marker attachments 122 is to provide a mechanical structure to mount or incorporate the markers securely on to the struts of segment 100, yet to maintain a smooth transition between the markers and the struts, so that the segment 100 can move smoothly when it is compacted inside a microcatheter.

Figure 3:
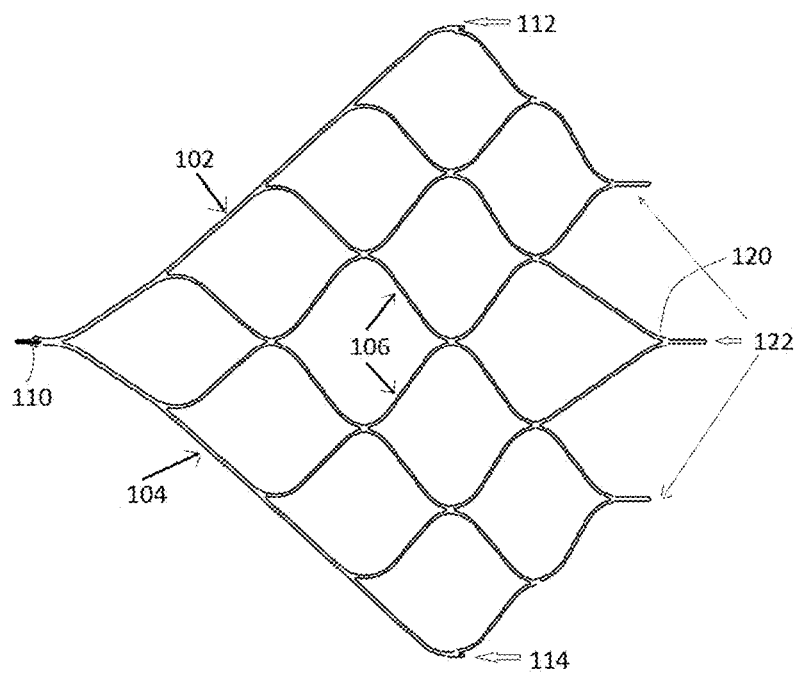
FIG. 3 is a two-dimensional view for the segment of FIG. 1 showing a modification thereto.

FIG. 3 shows a modification to the segment 100, where the marker attachments 122 can extend distally from the distal point 120 and/or the joints of the distal-most struts 106.

Even though FIG. 1 illustrates the segment 100 as having a certain configuration, the number of secondary struts 106 and cells 108 can be increased or decreased depending on the clinical application. For example, five secondary struts 106 can extend from each of the main struts 102 and 104, which would result in at least one additional column (e.g., P6—not shown) of cells 108 with column P5 having five cells 108 and column P6 having four cells 108. In addition, the segment 100 may change shape or dimensions along its length by varying the length and angle of the S-shaped struts 106. The size of the cell 108 can be also varied by varying the length and angle of the S-shaped struts 106. The three-dimensional diameter of the segment 100 can be varied by varying the number of cells 108, and the segment 100 may become thinner along its length. For example, the struts 106 of the segment 100 can be made narrower or thinner from the proximal to the distal direction within the same segment 100. Alternatively, if the clot removal device contains multiple segments 100 (as described below), the more distal segment(s) 100 can have narrower or thinner struts than the proximal segment 100, or vice versa. The diameter of the segment 100 can also be varied within the same segment 100. For example, in one segment 100, the distal end can have a diameter larger than that of the proximal end. If the clot removal device contains multiple segments 100, the more distal segment(s) 100 can have a larger diameter than that of the proximal segment 100, or vice versa.

FIG. 2 illustrates the segment 100 of FIG. 1 in three dimensions with the connecting points 112 and 114 joined or connected together so that the segment 100 has a generally tubular and/or tapered configuration across most of its longitudinal length. The segment 100 can be axially connected to another segment 100 to form a double segmented clot removal device (see FIGS. 7 and 8 below) or connected to the distal end of a delivery wire 128 (see FIG. 2). When attached to a delivery wire 128, the segment 100 can be introduced via an access catheter or microcatheter. The segment 100 can expand to a free diameter of 1.5 mm to 7.0 mm when pushed out of a catheter or microcatheter, or by holding the delivery wire 128 still and pulling the catheter or microcatheter proximately to release the segment 100, and each segment 100 can collapse into a compressed state of about 0.2 mm to 5.0 mm in diameter when pulled into the access catheter or microcatheter.

The segment 100 can be configured to act as a catch basket for the clot or embolus. Most significantly, the segment 100 as shown in FIG. 2 is not cylindrical in configuration which allows it to better conform to the tortuous vessel contour and to move more freely inside the vessel. The size of the distal opening 126 can range from 1.5 mm to 7.0 mm. The length of the segment 100 from the proximal point 110 to the distal point 120 can range from 5 mm to 30 mm. The length of the strut 106 can range from 0.5 mm to 20 mm. The length of the struts 102 and 104 can range from 10 mm to 50 mm. The size of the cells 108 can range from 0.25 mm$^2$ to 600 mm$^2$ The cells 108 and 124 themselves define a plurality of openings. During use, the blood clot can be caught by the struts of the cells 108 and 124, with portions of the clot sandwiched between the struts of cells 108 and 124 and the vessel wall to help to retain the clot to the segment 100. The size of the opening space (i.e., the cell size) is preferably sized to prevent the clot to break off from the segment 100.

A plurality of protrusions can be provided on the struts 102, 104, 106 by bending the struts outwardly. In addition, the struts 102, 104, 106 may include one or more surface modifications or treatments. For example, the surface of the struts may be roughened to improve clot adhesion, such as being mechanically or chemically treated to have a "rough" surface for improved clot adhesion. The "rough" surface can be achieved by (i) a porous surface coating or layer (ii) a micro blasted surface or micropinning, or (iii) an irregular strut geometry or arrangement.

The segment 100 can have a surface treatment on selected portions to improve performance for the selected portions of the segment 100. The segment 100 can either be coated or covered, entirely or partially, by typical biocompatible materials for clot retention and lubricity. The surface of the struts can have either a positive or negative charge for improved clot adhesion.

In addition, the main geometrical axis of the segment 100 can be offset or different from the longitudinal center axis of the native blood vessel. When the segment 100 is in use, both the delivery catheter (e.g., the microcatheter 130 in FIG. 4) and/or the movement axis of the segment 100 can be different from the longitudinal central axis of the vessel, and can contact the side wall of the blood vessel.

The segment 100 can be fully or partially coated with chemical(s), drug(s) or other bioagents to prevent clotting and/or for the better adhesion between the device and embolus. In addition, the surfaces of the segment 100 can be treated to form different surface layers (e.g., oxidation layer, Nitro or carbonized or N—C-combined surface layer, etc.) for better adhesion between the segment 100 and the embolus.

The delivery wire 128 can be made of super-elastic Nitinol wire, stainless steel wire, braided stainless steel wire, Co—Cr alloy and other biocompatible materials. The diameter of the delivery wire 128 can range from 0.008" to 0.030", and the delivery wire 128 can have variable diameters/stiffness along its length.

Figure 4:
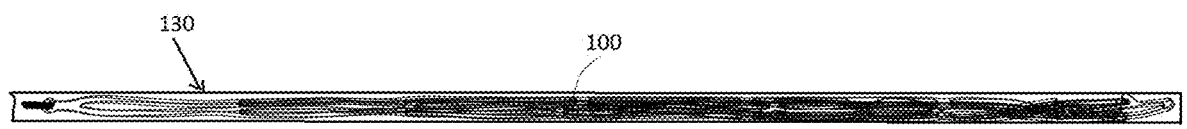
FIG. 4 illustrates the segment of FIG. 1 in a compacted configuration inside a microcatheter.
Figure 5:
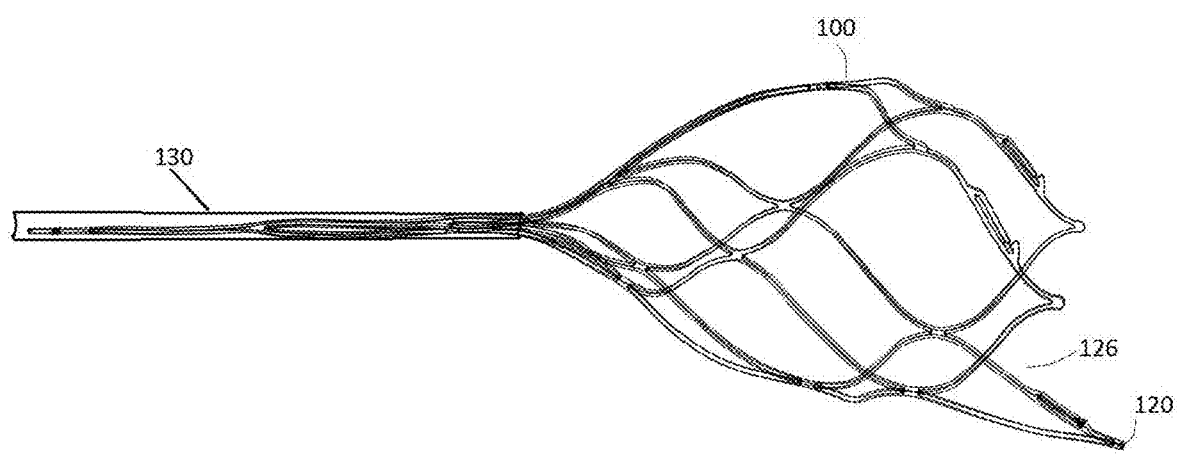
FIG. 5 illustrates the segment of FIG. 1 partially deployed from the microcatheter.
Figure 6:
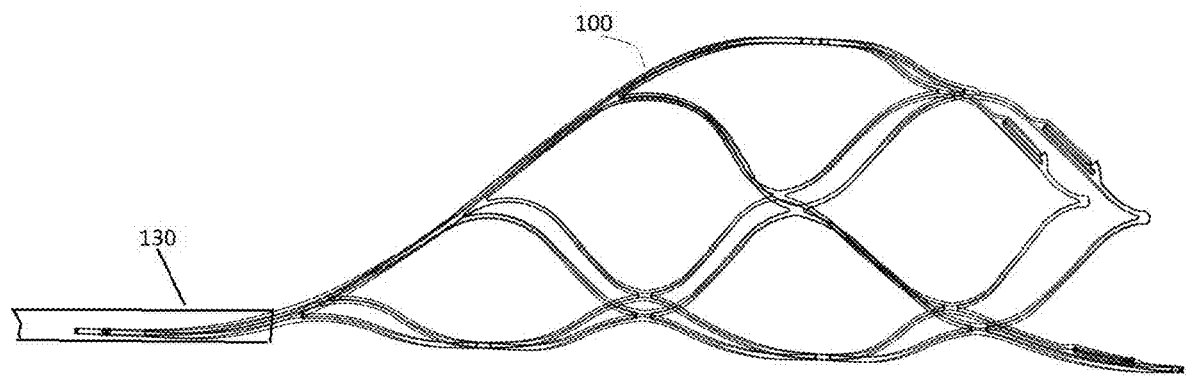
FIG. 6 illustrates the segment of FIG. 1 fully deployed from the microcatheter.

FIG. 4 shows the segment 100 compressed and fitted inside a microcatheter 130. In use, a guide wire can be inserted through the vasculature to the target treatment site, and then the microcatheter 130 is delivered over the guide wire to a target location in a vessel. The guidewire is then removed, and the segment 100 is advanced to the target treatment location through the lumen of the microcatheter 130 using conventional delivery techniques that are known to those skilled in the art. Alternatively, the microcatheter 130 can be inserted over the guide wire first, then the compacted segment 100 can be inserted through the inner lumen of the microcatheter 130. The distal end of the microcatheter 130 can be positioned on, or inside, or distal to, the clot or embolus at the target location, and there is no need for the microcatheter 130 to traverse the clot or embolus, thereby minimizing the possibility of pushing the clot or embolus downstream in the vessel. The microcatheter 130 can then be pulled back (proximally) to first expose the distal end of the segment 100 (see FIG. 5), and then the rest of the segment 100, until the proximal point 110 is also exposed outside of the microcatheter 130. See FIG. 6. Alternatively, the segment 100 can be pushed out of the microcatheter 130 via its proximal point 110.

Figure 7:
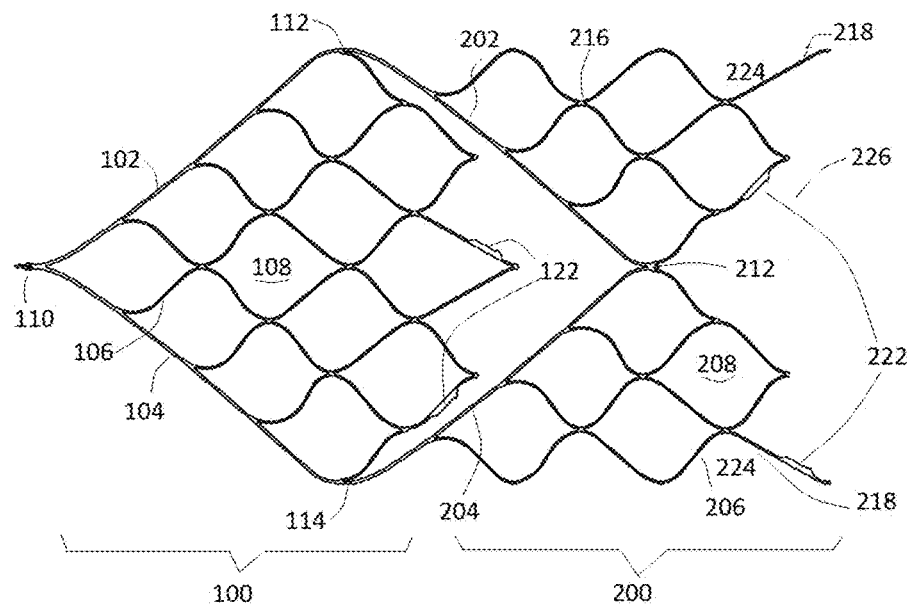
FIG. 7 is a two-dimensional view of a clot removal device having two segments according to a second embodiment of the present invention shown with the segments flattened.
Figure 8:
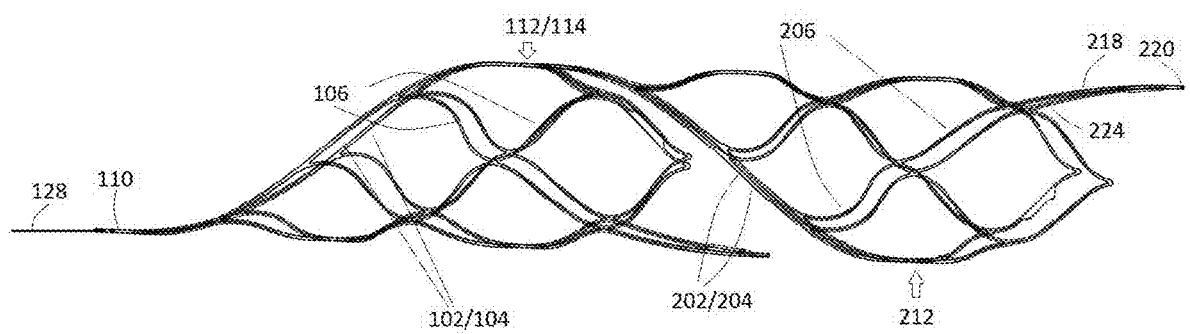
FIG. 8 is a three-dimensional view illustrating the segments of FIG. 7 with the segments connected at their connecting points.

FIGS. 7-8 illustrate a double-segment clot removal device which has two segments 100 and 200. The segment 100 is identical to the segment 100 shown and described above, and the segment 200 includes two main struts 202 and 204 having proximal ends connected to the connecting points 112 and 114, respectively. The distal ends of the main struts 202 and 204 are joined at a connecting point 212. The secondary struts 206 are arranged into a pattern to form a lattice of cells 208. Four secondary struts 206 extend from each main strut 202 and 204, including one pair of secondary struts 206 that extend from the connecting point 212. Each secondary strut 206 also has a straight section with opposite ends that are slightly curved in opposite directions so as to form an S-shape. The secondary struts 206 are joined at connection points 216 to form cells 208 that have a teardrop-like shape due to the S-shaped configuration of the secondary struts 206. Two generally straight distal struts 218 extend from the distal end of the segment 200, and their proximal ends are connected to each other to form a cell 224, and their distal ends are connected to each other form a tip 220. See FIG. 8. A distal opening 226 is defined by the distal cells 208 and 224.

In the embodiment in FIG. 7, the segment 200 has four secondary struts 206 extending from each main strut 202 and 204, and the resulting lattice of cells 208 defines a row of four cells 208 along each main strut 202 and 204. Another row of three cells 208 extends parallel to, and side-by-side with, the row of four cells 208 on either side of the connecting point 212.

Another way to view this lattice is that the connected secondary struts 206 that extend from the main struts 202 and 204 define waveforms. For example, the proximal-most secondary struts 206 extending from the main struts 202 and 204 each define the beginning of a first waveform of four secondary struts 206, and terminate at a connection with a distal strut 218. The second proximal-most secondary struts 206 extending from the main struts 202 and 204 each define the beginning of a second waveform of four secondary struts 206, and the third proximal-most secondary struts 206 extending from the main struts 202 and 204 each define the beginning of a third waveform of three secondary struts 206.

The segment 200 can also be marked with coils, tubes, wires or other markers made of radiopaque, or x-ray blocking, materials such as platinum, gold, or other dense materials. As an example, radiopaque marker attachments 222 can be provided on any of the struts 202, 204, 206 or 218. These markers can be made of Ta, Pt, W, Pt—W, or Pt—Ir alloys for radiopacity, and from radiopaque coils or markers.

Even though FIG. 7 illustrates the segment 200 as having a certain configuration, the number of secondary struts 206 and cells 208 can be increased or decreased depending on the clinical application, as described above in connection with the segment 100.

FIG. 8 illustrates the segments 100 and 200 of FIG. 7 with the connecting points 112 and 114 joined or connected together so that the segment 100 has a generally three-dimensional tubular configuration across most of its longitudinal length, and with the connecting point 212 joined so that the segment 200 has a generally tubular configuration across most of its longitudinal length. The segment 200 can be provided with any of the other features (e.g., surface coatings, surface modifications, etc.) described above in connection with segment 100. In this embodiment, the segments 100, 200 are opposed by 180 degrees, and connected in a helical or multiple helix configuration.

Figure 9:
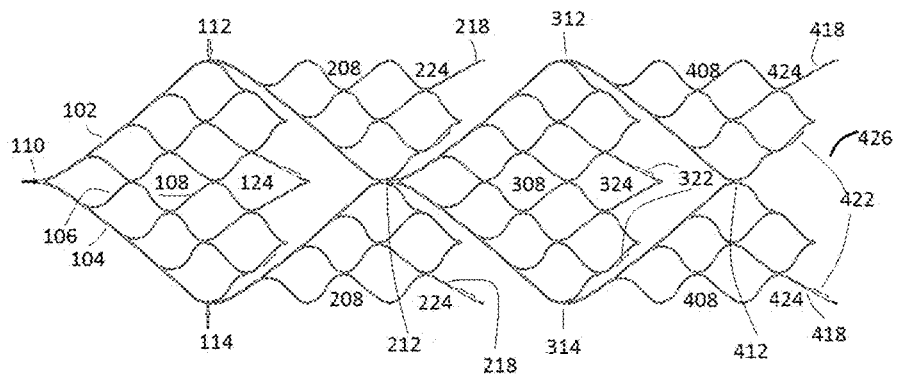
FIG. 9 is a two-dimensional view of a clot removal device having four segments according to a third embodiment of the present invention shown with the segments flattened.
Figure 10:
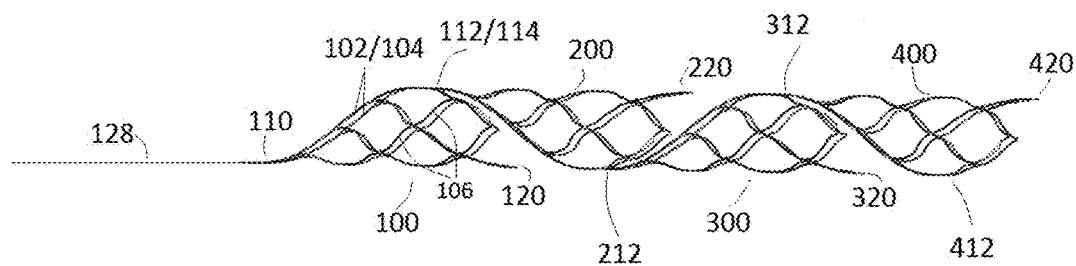
FIG. 10 is a three-dimensional view illustrating the segments of FIG. 9 with the segments connected at their connecting points.

FIGS. 9-10 illustrate a multi-segment clot removal device which has four segments 100, 200, 300 and 400. The segments 100 and 200 are identical to the segments 100 and 200, respectively, shown and described above, and the segments 300 and 400 can be the same as segments 100 and 200, respectively. Thus, the same elements in the segments 100 and 300 have the same last two digits in their numerals but differ in that the first digit is either a "1" or "3". In other words, the elements 108 and 308 in the two segments 100 and 300, respectively, are the same, and so on. The same numbering convention applies to the segments 200 and 400. In the embodiment shown in FIGS. 9 and 10, the proximal point for the segment 300 is actually connected to the connecting point 212, otherwise the construction and connections for segments 300 and 400 are the same as for segments 100 and 200.

Figure 11:
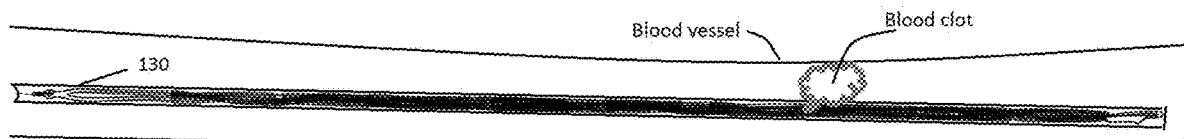
FIG. 11 illustrates the segments of FIG. 9 in a compacted configuration inside a microcatheter inside a blood vessel.

FIG. 11 shows the clot removal device of FIGS. 9 and 10, with its four segments 100, 200, 300 and 400 compressed and fitted inside a microcatheter 130. In use, a guide wire can be inserted through the vasculature to the target treatment site, and then the microcatheter 130 is delivered over the guide wire to a target location in a vessel with the segments 100,200,300, and 400 housed therein using conventional delivery techniques that are known to those skilled in the art. Alternatively, the microcatheter 130 can be inserted over the guide wire first, and then the guide wire can be removed. Next, the compacted segments 100, 200, 300 and 400 can be inserted through the inner lumen of the microcatheter 130. The distal end of the microcatheter 130 can be positioned inside, or distal to, the clot or embolus at the target location, and there is no need for the microcatheter 130 to traverse the clot or embolus, thereby minimizing the possibility of pushing the clot or embolus downstream in the vessel.

Figure 12:
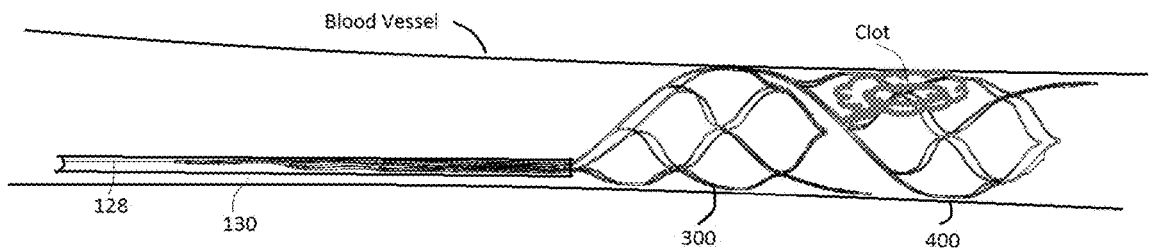
FIG. 12 illustrates the segments of FIG. 9 partially deployed from the microcatheter.
Figure 13:
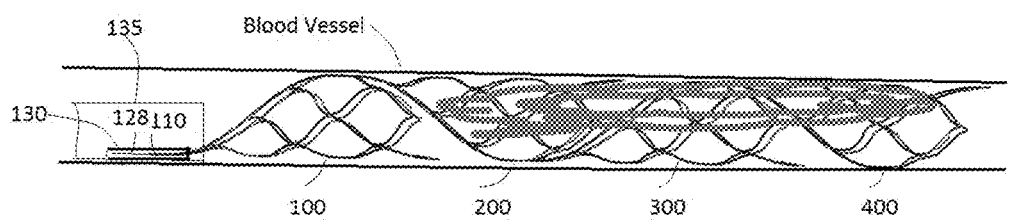
FIG. 13 illustrates the segments of FIG. 9 fully deployed from the microcatheter and engaging a lengthy blood clot.
Figure 14:
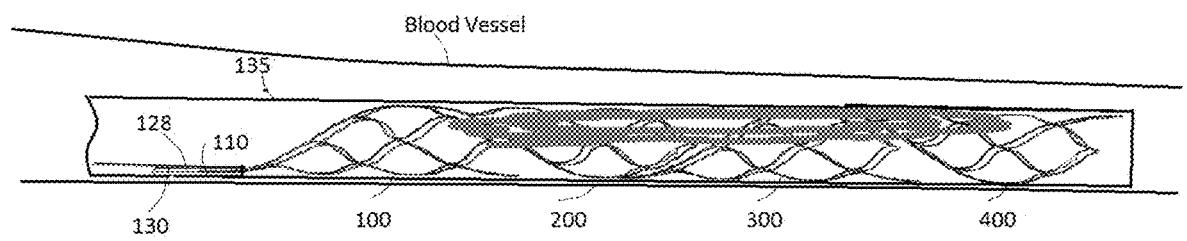
FIG. 14 illustrates the segments of FIG. 9 fully withdrawn into the guide catheter with the blood clot engaged therein.

Next, the microcatheter 130 can then be pulled back (proximally) to first expose the distal-most segment 400, and then pulled back further to expose the next distal-most segment 300. See FIG. 12. Alternatively, the segment 100 can be pushed out of the microcatheter 130 via its proximal point 110, which causes the segment 400 to be pushed out first, followed by the other segments 300, 200 and 100, in this order. At this point, referring to FIG. 13, the blood clot is gripped or grasped by the segments 200, 300 and 400. The segments 100, 200, 300 and 400 can then be retracted into the guide catheter 135 (see FIG. 14) to pull the blood clot into the guide catheter 135. This retraction can be done without the segments 100, 200, 300 and 400 re-entering the microcatheter 130, and in fact, the microcatheter 130 is pulled proximally in the guide catheter 135 to facilitate this retraction. During the clot retrieval process, suction/aspiration can be applied through the lumen of the access devices (e.g., the guide catheter 135, or microcatheter 130) and the encapsulation of the segment 200 (with clot engaged) can happen either simultaneously or in sequence during the procedure.

The clot removal device with single segment 100 can be used to remove the shorter or smaller clots, whereas the clot removal devices with multiple segments can be used to remove the larger or longer clots. The physician can determine the length of the clot under fluoroscopy or other imaging, and then select a clot removal device having the desired number of segments.

While the description above refers to particular embodiments of the present invention, it will be understood that many modifications may be made without departing from the spirit thereof. The accompanying claims are intended to cover such modifications as would fall within the true scope and spirit of the present invention.

What is claimed is:

1. A clot removal device, comprising a plurality of segments that includes at least a first segment and a second segment, each segment having two main struts that serve as a supporting frame that is connected to a plurality of secondary struts, wherein:
the plurality of secondary struts form a lattice of cells for each segment;
the two main struts of the first segment having proximal ends that are connected to each other at a proximal point of the first segment, and distal ends terminating at separate connecting points that are distal from the proximal point, with the connecting points being connected to each other to form a generally tubular structure defining an inner lumen for the first segment; and
the two main struts of the second segment having proximal ends, each being connected to a separate one of the distal ends of the two main struts of the first segment at the connecting points, and the main struts of the second segment also having distal ends that are connected to each other in the second segment; and wherein the clot removal device is delivered to a location at or adjacent to a clot or embolus in the blood vessel, and the plurality of segments are expanded at or adjacent the location of the clot or embolus.

2. The device of claim 1, wherein the first segment has two generally straight distal struts that are connected to the lattice of cells at a distal end of the segment, and are connected to each other to form a distal point, thereby defining a first segment distal opening by the cells adjacent the distal struts, with the first segment distal opening communicating with the lumen and terminating at the proximal point.

3. The device of claim 1, wherein each secondary strut has a straight section having opposite ends that are slightly curved in opposite directions so as to form an S-shape, with the secondary struts joined at connection points to form the cells.

4. The device of claim 3, wherein the cells have a tear-drop-like shape.

5. The device of claim 2, wherein the second segment comprises two generally straight second segment distal struts extending distally from a distal end of the second segment to define a second segment distal opening, and wherein the first segment distal opening and second segment distal opening are axially offset by 180 degrees.

6. A clot removal device, comprising a plurality of segments that includes at least a first segment, a second segment and a third segment, each segment having two main struts that serve as a supporting frame that is connected to a plurality of secondary struts, wherein:

the plurality of secondary struts form a lattice of cells for each segment;

the two main struts of the first segment having proximal ends that are connected to each other at a proximal point of the first segment, and distal ends terminating at separate first segment connecting points that are distal from the proximal point, with the first segment connecting points being connected to each other to form a generally tubular structure defining an inner lumen for the first segment;

the two main struts of the second segment having proximal ends, each being connected to a separate one of the distal ends of the two main struts of the first segment at the first segment connecting points, and the main struts of the second segment also having distal ends that are connected to each other in the second segment; and the two main struts of the third segment having proximal ends that are connected to each other at a proximal point of the third segment, and to the distal ends of the two main struts of the second segment, the two main struts of the third segment also having distal ends terminating at separate third segment connecting points that are distal from the proximal point, with the third segment connecting points being connected to each other to form a generally tubular structure defining an inner lumen for the third segment;

wherein the clot removal device is delivered to a location at or adjacent to a clot or embolus in the blood vessel, and the plurality of segments are expanded at or adjacent the location of the clot or embolus.

7. The device of claim 6, wherein the first segment has two generally straight distal struts are connected to the lattice of cells at a distal end of the segment, and are connected to each other to form a distal point, thereby defining a first segment distal opening by the cells adjacent the distal struts, with the first segment distal opening communicating with the lumen and terminating at the proximal point.

8. The device of claim 6, wherein each secondary strut has a straight section having opposite ends that are slightly curved in opposite directions so as to form an S-shape, with the secondary struts joined at connection points to form the cells.

9. The device of claim 8, wherein the cells have a tear-drop-like shape.

10. The device of claim 7, wherein the second segment comprises two generally straight second segment distal struts extending distally from a distal end of the second segment to define a second segment distal opening, wherein the first segment distal opening and second segment distal opening are axially offset by 180 degrees.

11. The device of claim 6, wherein the plurality of segments further includes a fourth segment having the two main struts, each having proximal ends that are connected to a separate one of the distal ends of the two main struts of the third segment at the third segment connecting points, and the main struts of the fourth segment also having distal ends that are connected to each other in the fourth segment.

* * * * *